United States Patent [19]

Ou

[11] Patent Number: 5,442,040
[45] Date of Patent: Aug. 15, 1995

[54] EXTRACTION OF SELECTION HYDROCARBONS FROM A HYDROCARBON STREAM USING A CARBON ADSORBENT

[75] Inventor: John D.-Y. Ou, Houston, Tex.

[73] Assignee: Exxon Chemical Patents Inc., Linden, N.J.

[21] Appl. No.: 178,713

[22] Filed: Jan. 10, 1994

Related U.S. Application Data

[63] Continuation-in-part of Ser. No. 982,137, Nov. 24, 1992, abandoned, which is a continuation of Ser. No. 554,305, Jul. 17, 1990, abandoned.

[51] Int. Cl.$^6$ ............................................. C07C 7/12
[52] U.S. Cl. .................... 528/482; 585/820; 585/829
[58] Field of Search ............... 528/482; 585/820, 829

[56] References Cited

U.S. PATENT DOCUMENTS

| | | | |
|---|---|---|---|
| 2,765,914 | 10/1956 | Seyfried | 210/42.5 |
| 3,725,377 | 4/1973 | Cottle | 260/94.2 R |
| 4,570,029 | 2/1986 | Kulprathipanja et al. | 585/829 |
| 4,734,273 | 3/1988 | Haskell | 423/219 |

FOREIGN PATENT DOCUMENTS

0371692A2  6/1990  European Pat. Off. .

OTHER PUBLICATIONS

Kirk–Othmer Encyclopedia of Chemical Technology, Fourth Edition, vol. 8, pp. 944–955 (1994).
Hawley's Condensed Chemical Dictionary, 8th Edition, pp. 218–219 (1987).

Primary Examiner—David W. Wu
Attorney, Agent, or Firm—Linda K. Russell

[57] ABSTRACT

The present invention is directed to adsorbing polymeric hydrocarbons (ie. polymers of iso-butylene, polymers of the isomers of iso-butylene (poly-butenes) and co-polymers of iso-butylene and other olefins (butyl rubber) from hydrocarbon or raffinate streams using activated carbon as the adsorbent. One embodiment includes the selective removal of poly-isobutylene (PIB) from a hydrocarbon stream by activated carbon. The stream which can exceed 100 ppm PIB is contacted with the activated carbon for a sufficient time to reduce the PIB content of the hydrocarbon stream to less than about 1 ppm.

28 Claims, 2 Drawing Sheets

EXTRACTION OF SELECTION HYDROCARBONS FROM A HYDROCARBON STREAM USING A CARBON ADSORBENT

CROSS REFERENCE TO RELATED APPLICATIONS

This application is a continuation-in-pan of application Ser. No. 07/982,137 filed Nov. 24, 1992, now abandoned, which is a continuation of 07/554,305 filed Jul. 17, 1990, now abandoned.

BACKGROUND OF THE INVENTION

1. Field of the Invention

The present invention relates to extraction of selected hydrocarbons from mixed hydrocarbon and raffinate streams using carbon. More particularly, the present invention is directed to adsorbing polymeric hydrocarbons from hydrocarbon or raffinate streams using activated carbon as the adsorbent. Specifically, the present invention is directed to the extraction of poly-isobutylene from $C_4$ and/or $C_5$ raffinate using activated carbon as the adsorbent.

2. Discussion of Background and Material Information

Steam cracked naptha produces several product streams including a $C_4$ raffinate stream. This $C_4$ stream is a mixture of four carbon hydrocarbons and can be used in the production of methyl tert-butyl ether (MTBE) or poly-isobutylene (PIB). In MTBE production, the process steps include adding methanol to the $C_4$ raffinate stream to produce MTBE and subsequent recovery of methanol. In the PIB process, the $C_4$ stream is contacted to an acidic catalyst to convert isobutylene to poly-isobutylene. At steps during the PIB process a second $C_4$ raffinate stream is recovered. This $C_4$ stream typically contains butene-1, butene-2, isobutylene, n-butane, isobutane, and a low level of impurities including a small amount of PIB.

A $C_4$ stream with a small PIB content, however, is considered unacceptable for MTBE production due in part to the high boiling point of PIB. Related to this, even small quantities, in parts per million, have been observed to plug a methanol recovery column in a processing plant and cause a gram/mole to more than 2,500 gram/mole with a typical weight of 900 gram/mole.

Distillation separation of PIB from the second $C_4$ stream is impractical because of the relatively low levels of PIB present, the relatively high molecular weight of PIB, and because PIB is relatively visous and has a high boiling point relative to the $C_4$ isomers.

U.S. Pat. No. 3,725,377, Cottle, assigned to Phillips Petroleum Company, is directed to a process for polymerizing monomers which involves contacting the polymerizing monomers which involves contacting the polymerization feedstock stream with an adsorbent material to remove non-polymerizable hydrocarbons separated from the feedstock stream. More specifically, Cottle discloses the clean-up of butadiene for anionic polymerization, although he also discloses that the process can be used to purify other olefinic, dienic, styrenic streams, and even hydrocarbon solvents. Cottle begins his process by partially purifying the feed by hydrogenation and fractional distillation, and then contacts the resultant stream with an adsorbent which may be activated carbon. Although isobutylene is a component of the stream used in the example, as indicated in the Table, there is no teaching or suggestion that poly-isobutylene is a contaminant in the stream, or that poly-isobutylene would be adsorbed by the activated carbon.

U.S. Pat. No. 2,765,914, Seyfried, assigned to Esso Research and Engineering Company, is directed to a method for removing free sulfur from liquefied hydrocarbon gas, and more specifically by removing the elemental sulfur by adsorption of the sulfur on adsorbent carbon. Seyfried discloses treating a $C_1$-$C_6$, non-aromatic, liquefiable hydrocarbon with activated carbon to remove sulfur. Although $C_1$-$C_6$, non-aromatic, liquefiable hydrocarbons are broadly disclosed and claimed, liquefied petroleum gas is disclosed as being most preferred for purposes of treatment in accordance with the invention disclosed by Seyfried. Seyfried does not teach or suggest the attraction of branched-chain hydrocarbons, or poly-isobutylene, using activated carbon.

U.S. Pat. No. 4,734,273, Haskell, assigned to Shell Oil Company, is directed to a process for selectively sorbing trace amounts of oxygen from low molecular weight olefins and inert gases by contacting with high surface area particulate coal-derived activated carbon having high ash and moisture contents. 1- and 2-butene and isobutene are disclosed as being suitable for this process; and the oxygen which is removed is originally present in concentrations up to about 10 ppm. There is no teaching or suggestion that the activated carbon adsorbent would be effective to remove branched-chain hydrocarbons or poly-isobutylene from raffinate streams.

In the past, therefore, the PIB contaminated streams normally have been discarded because of the associated processing difficulties. It would be desirable if objectionable amounts of PIB could be removed to produce a substantially PIB-free $C_4$ stream which could be utilized in further processing.

SUMMARY OF THE INVENTION

The present invention is based on the discovery that the adsorption characteristics of carbon are particularly suitable for removing selected hydrocarbons from mixed hydrocarbon streams.

In this regard, it has been discovered that carbon unexpectedly adsorbs polymeric hydrocarbons, for example, polymers of iso-butylene (poly-isobutylenes), polymers of the isomers of iso-butylene (poly-butenes) and co-polymers of iso-butylene and other olefins (butyl rubber), preferentially over non-polymeric hydrocarbons, for example, butene, which are often present in mixed hydrocarbon streams.

The discovery of the present invention is particularly effective for removing, extracting, adsorbing or otherwise separating selected hydrocarbons, i.e., polymeric hydrocarbons, e.g., poly-isobutylene, from $C_4$ and/or $C_5$ hydrocarbon streams.

The present invention advantageously uses the discovery that the carbon adsorbent has more affinity for a higher molecular weight hydrocarbons, such as branched-chain hydrocarbons, i.e., poly-isobutylene, which have a higher molecular weight, e.g., within the range of about 112 gram/mole to about 2,500+ gram/mole, with a majority in the 900 gram/mole region, than lower molecular weight $C_4$ isomers, e.g., less than 58 gram/mole.

In accordance with a preferred embodiment of the present invention, the process of this invention involves removing PIB from a $C_4$ and/or $C_5$ hydrocarbon stream, such as a raffinate stream, by contacting the stream with activated carbon for adsorption of the PIB.

In accordance with the present invention, therefore, mixed hydrocarbon streams which contain PIB, including $C_4$ streams, $C_5$ streams or a mixture of both $C_4$ and $C_5$ streams, are exposed to or otherwise contacted with carbon for a sufficient time to permit selected adsorption of the PIB. Activated carbon adsorbs PIB with a greater affinity than the other components and isomers of the $C_4$ or $C_5$ stream.

DETAILED DESCRIPTION OF THE INVENTION

Figure 1:
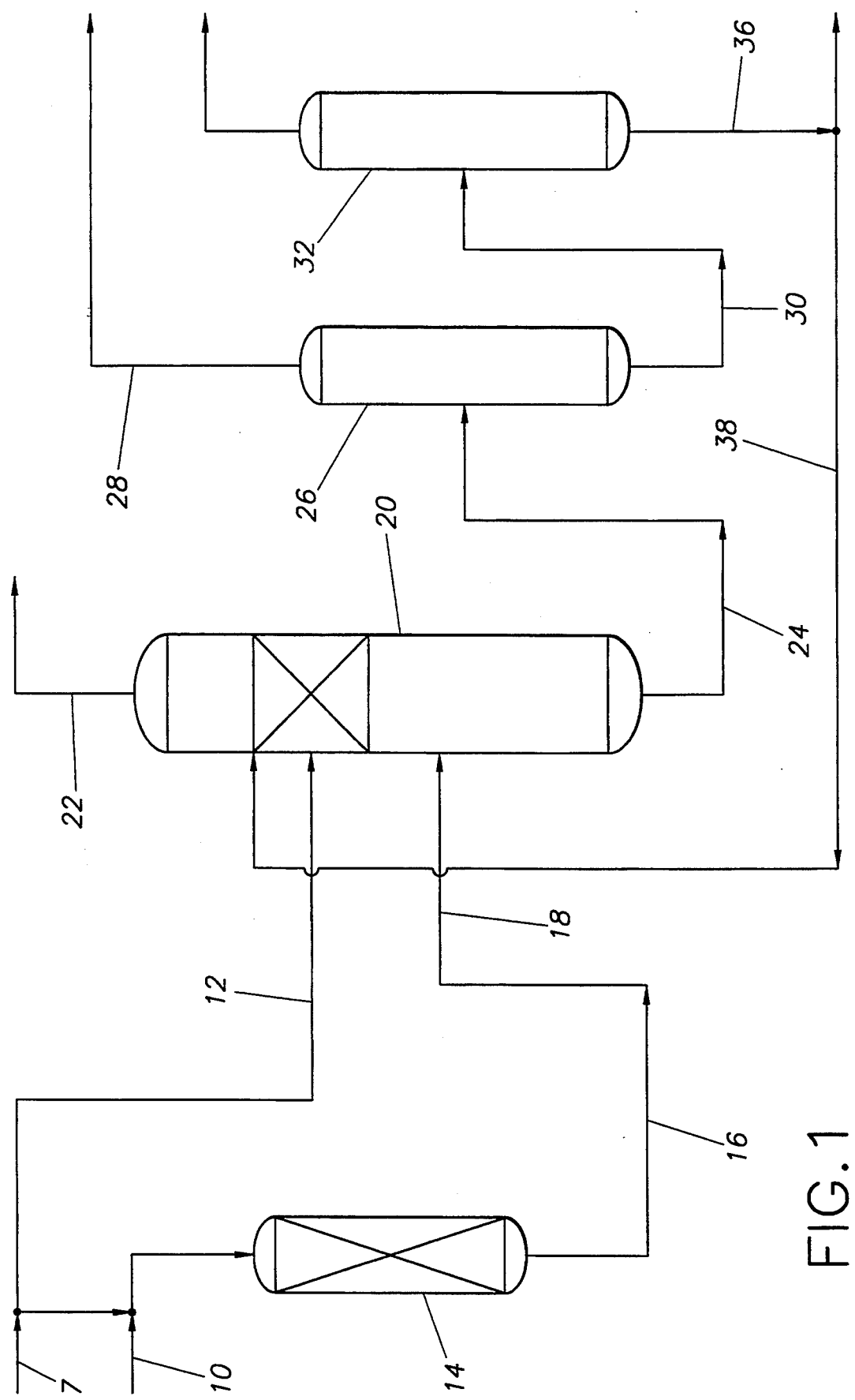
FIG. 1 is a flow chart for the adsorption process of the present invention.

In general, the present invention is directed to a process for treating a mixed hydrocarbon or raffinate stream by the selective separation of hydrocarbons having certain characteristics from the mixed hydrocarbon and raffinate streams wherein the process involves contacting the stream which includes an amount of selected hydrocarbons having certain characteristics which are to be removed from the stream, also referred to herein as undesirable hydrocarbons, with carbon under adsorption conditions and for a time effective for adsorption of such undesirable hydrocarbons from the stream to produce a resultant stream having a reduced amount of the undesirable hydrocarbons.

The carbon preferred for purposes of the present invention has at least one characteristic selected from the group consisting of a surface area within the range of about 50 $m^2/g$ to about 2000 $m^2/g$ and a pore volume within the range of about 0.2 cc/g to about 1 cc/g; with a surface area within the range of about 500 $m^2/g$ to about 1200 $m^2/g$, and with a range of about 500 $m^2/g$ to about 1200 $m^2/g$, and with a pore volume within the range of about 0.6 cc/g to about 1 cc/g being preferred; and a surface area within the range of about 1000–1100 $m^2/g$ and a pore volume of about 0.88 $m^2/g$ being most preferred. The carbon may be in a form selected from the group consisting of granular activated carbon and powdered activated carbon, although granular activated carbon is preferred. Also, the carbon adsorbent may be placed in a fixed bed, column, canister, or any other suitable configuration, which permits the passage of the hydrocarbon of raffinate stream there through so as to permit exposure and contact of the hydrocarbon or raffinate stream with the carbon adsorbent for effective adsorption of the undesirable hydrocarbons from the hydrocarbon or raffinate stream. The amount of carbon used depends on the surface area and pore size of the carbon selected and the amount of PIB in the stream. For purposes of the present invention, it is preferable to use an activated carbon having characteristics as described above as the adsorbent. Representative examples of activated carbon preferred for purposes of the present invention are commercially available as CAL, OL, SGL from Calgon Carbon Corp.; as PETRODARCO from American Norit Co.; and as NUCHAR from Westvaco. The activated carbon absorbent more preferred for purposes of the present invention has a pore volume within the range of about 0.6 to 1 cc/g. Typically 0.09 Kg to 0.45 Kg of the preferred activated carbon is used per 450 Kgs of $C_4$ stream containing 50 ppm of PIB. The amount of activated carbon can be adjusted based on the PIB content of the stream.

The carbon adsorbent is preferably maintained at a temperature within the range of about 10° C. to about 100° C. and more preferably within the range of about 25° C. to about 65° C. during processing in accordance with the present invention.

Although the mixed hydrocarbon and raffinate streams may be processed in accordance with the present invention in their liquid phase or in their vapor phase, it is preferable to treat liquid hydrocarbon or raffinate streams with activated carbon in order to remove selected undesirable hydrocarbons from the mixed hydrocarbon or raffinate stream in accordance with the present invention. For purposes of the present invention, a $C_4$ and/or $C_5$ raffinate stream is preferred with a $C_4$ raffinate stream being most preferred.

The process of the present invention is preferably performed under a pressure within the range of about 50 psi to about 500 psi, and most preferably at about 300 psi.

In accordance with the present invention, the hydrocarbon or raffinate streams are preferably passed through a bed or other configuration of the activated carbon at a flow rate within the range of about 0.1 LHSV to about 2.0 LHSV, and preferably at a flow rate of about 0.2 LHSV to about 1.0 LHSV.

The invention may also be used to separate polymeric hydrocarbons having a molecular weight within the range of about 100gram/mole to 2000 gram/mole, or more, from mixed hydrocarbon streams. Examples of polymeric hydrocarbons with this particular weight include poly-propylene, poly-butene, and poly-isobutylenes. Of particular interest are the $C_4$ polymers of isobutylene (poly-isobutylenes), polymers of the isomers of isobutylene (poly-butenes) and co-polymers of iso-butylene and other olefins (butyl rubber). In addition to that similarity in molecular weight, these polymers have similar structures, chemical reactivities, solution properties, physical properties and end uses as plasticizers. It has been discovered invention is most preferred for use in separating poly-isobutylene from $C_4$ and or $C_5$ raffinate streams.

The process of the present invention has been discovered to be particularly effective in separating selected or undesirable hydrocarbons which are present within the mixed hydrocarbon or raffinate stream in an amount within the range of up to about 2% but preferably within the range of about 50 ppm to about 600 ppm, and most preferably within the range of about 50 ppm to about 100 ppm, so as to result with a resultant stream containing less than about 5 ppm and preferably less than about 1 ppm of the selected or undesirable hydrocarbon. The process of the present invention is most effective for removing up to about 100 ppm poly-isobutylene from a hydrocarbon stream including $C_4$ and $C_5$ hydrocarbons.

The present invention has been discovered to be most effective in a fixed bed operation.

In accordance with the present invention, as described above, a hydrocarbon stream contaminated with poly-isobutylene is pumped through a column packed with activated carbon adsorbent at a temperature ranging from about ambient to about 65° C., a pressure of about 300 psig, and a flow rate of about 0.2 to about 1 LHSV to produce a resultant stream typically containing less than about 1 ppm of poly-isobutylene.

FIG. 1 of the accompanying drawing, which is presented as a representative example of the present invention for illustrative purposes, and is not meant to limit the present invention to the details shown and described, is a flowsheet of the process for the removal of selected hydrocarbons in accordance with the present invention.

As shown, the charge stock (containing normal butenes, isobutylene, butanes, and low level of butyl chlorides and poly-isobutylene) to be treated for poly-isobutylene removal is the raffinate stream from the fractionation tower 2 of a poly-isobutylene unit 1. The stream containing 50 ppm to 2% poly-isobutylene is introduced into the adsorption column 3, purposes of removing the poly-isobutylene from the raffinate stream. The effluent from the adsorption column, which contains less than about 1 to 5 ppm poly-isobutylene, can then be used as a feedstock for a down-stream methyl tertiary butyl ether (MTBE) unit 4.

Figure 2:
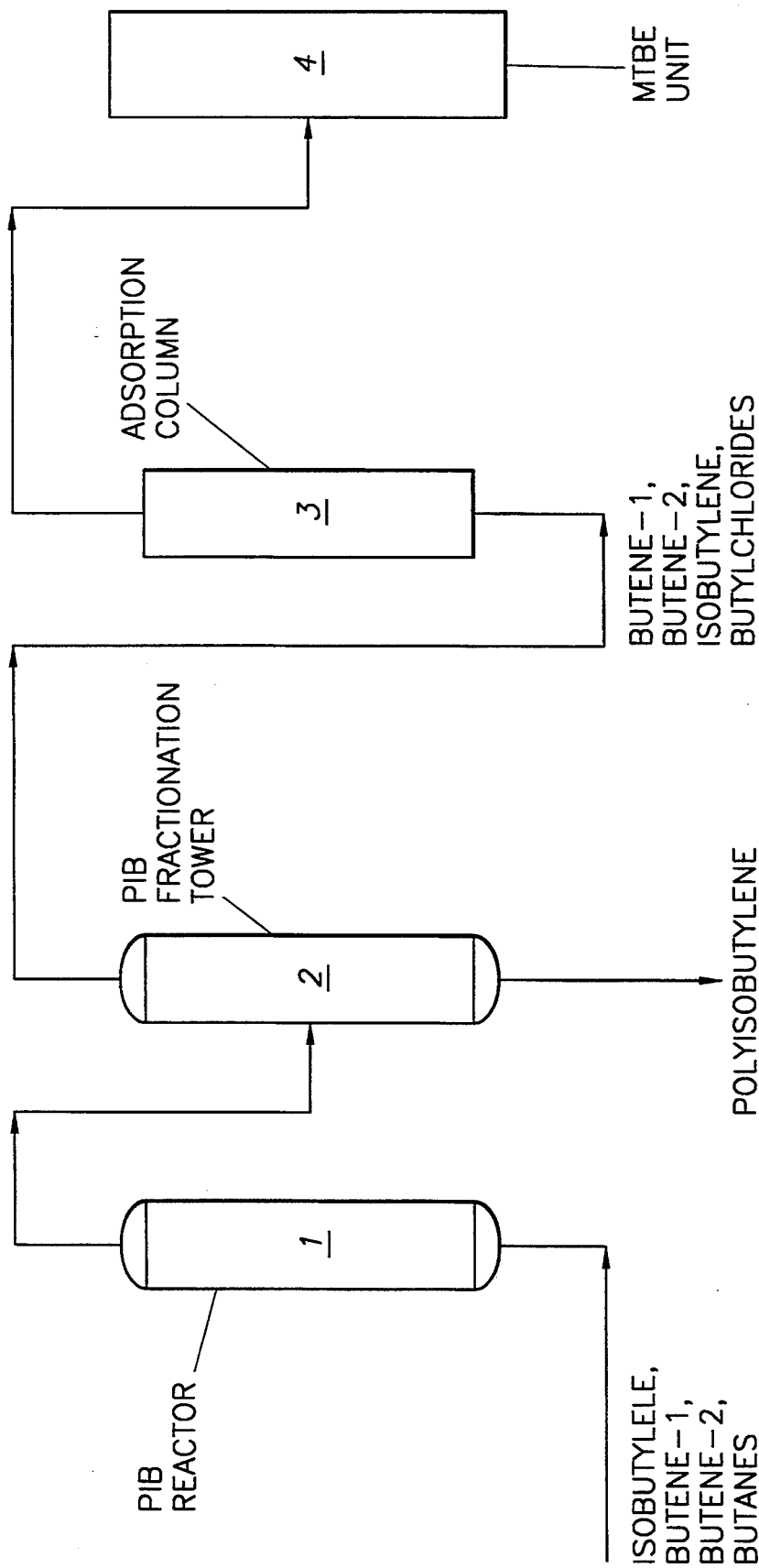
FIG. 2 is a flow chart for a process of the production of MTBE, for example as depicted in FIG. 1.

In this regard, the present invention finds utility in removing poly-isobutylene from a raffinate stream to be used in any conventional process for the production of MTBE, for example, as disclosed in U.S. Pat. No. 4,307,254, the disclosure of which is hereby incorporated in its entirety by reference hereto. Referring, however, now to FIG. 2, a schematic system is shown which can be used to produce MTBE.

A feedstream 7 containing a stoichiometric amount of methanol, based on isobutylene, is introduced together with an isobutylene containing feedstream 10 to a lead synthesis reactor 14. The lead synthesis reactor 14 is provided with an acidic resin catalyst, such as Amberlyst-15 (trademark), Dowex DR-2040, Lewatit SPC 18 BG, or Dowex M-31, and is heated to an appropriate temperature. The effluent or product stream 16 leaving the reactor is composed of MTBE, unreacted hydrocarbons and methanol (MeOH). The resultant product stream is the feedstream 18 which is then fed to a distillation column 20. The vaporized overhead 22 is composed of raffinate depleted in olefins branched at the point of unsaturated (sometimes referred to as tertiary olefins which is passed through methanol removal and final clean-up procedures). As disclosed in commonly owned co-pending application U.S. Ser. No. 274,557, now abandoned a stream 12 of methanol is introduced into the catalytic distillation reaction zone. The effluent is then passed to a product topping tower 26 wherein effluent is then passed to a product topping tower 26 wherein $C_5$ hydrocarbons are removed for separate processing. The resultant effluent stream 30 is then passed to product tailing tower wherein MTBE is removed as product. The effluent 36 from tailing tower contains various components including oxygenates, such as TAME, which may be recycled to a conduit 38 to supply oxygenate to the catalyst reaction zone.

Other catalytic distillation processes, such as those disclosed in U.S. Pat. No. 4,232,177, 4,307,254, and 4,336,407, SMITH, Jr., have been developed to improve the recovery of MTBE, and are suitable processes for modification by the process in accordance with the present invention. The disclosures of U.S. Pat. No. 4,232,177, 4,307,254, and 4,336,407, also are, therefore, hereby incorporated in their entirety herein by reference.

A $C_4$ stream typically contains up to or exceed 100ppm PIB. However, a PIB content of less than about 1 ppm in a $C_4$ feedstock is desirable for downstream processing, such as MTBE production. In accordance with the present invention, the activated carbon effectively reduces the PIB content of such raffinate streams to less than 1 ppm.

EXAMPLE 1

A $C_4$ raffinate stream of 40% butene-1, 23% butene-2, 35% n-butane and isobutane, 2% isobutylene with 50 ppm PIB was contacted to Calgon Type OL granular carbon (20/50 mesh). The Calgon Type OL granular carbon has a total surface area of 1000–1100 $m^2$ and pore volume of 0.88 cc/g. The $C_4$ stream and activated carbon were allowed to equilibrate at a 13:1 volume ration, respectively, at room temperature of 22° C. at 300 psi pressure.

At 18 hours of equilibration the amount of PIB in the $C_4$ raffinate was less than 5 ppm.

EXAMPLE 2

A $C_4$ raffinate stream containing 12.9% butene-1, 9.5% butene-2, 3.9% isobutylene, 70.6% n-butane, 1.2% isobutane and 1.9% PIB was contacted to Calgon Type OL carbon. The contaminated $C_4$ stream was pumped through five, 200 cc columns of activated carbon connected in series at an overall flow rate of 0.2 LHSV (Liquid Hourly Space Velocity) at room temperature of about 26° C. and 300 psi.

The product collected at the outlet of the last column contained less than 1 ppm before the amount of PIB adsorbed on the activated carbon reached 8.1% wt. of the carbon.

Although the invention has been described with reference to particular means, materials, and embodiments, from the foregoing description, one skilled in the art can easily ascertain the essential characteristics of the present invention, and various changes and modifications may be made to various usages and conditions, without departing from the spirit and scope of the invention as described in the claims that follow.

I claim:

1. A process for treating mixed hydrocarbon streams containing polymers involving the selective separation of polymers from the stream, said process comprising:
    contacting a hydrocarbon stream comprising an amount of polymers, with activated carbon under adsorption conditions and for a time effective for adsorption of said polymers from said hydrocarbon stream to produce a resultant stream having a reduced amount of said polymers, wherein said polymers are selected from the group consisting of poly-propylene, poly-iso-butylene, polymers of the isomers of iso-butylene, and co-polymers of iso-butylene and other olefins, wherein said amount of said polymers present in said stream in an amount within the range of about 50 ppm to 2%, and wherein said resultant stream contains less than 5 ppm of said polymers.

2. The process for treating mixed hydrocarbon streams of claim 1, wherein said carbon has a surface area within the range of about 50 $m^2/g$ to about 2000 $m^2/g$ and a pore volume within the range of about 0.2 cc/g to about 1 cc/g.

3. The process for treating mixed hydrocarbon streams of claim 2, wherein said surface area is within the range of about 500 $m^2/g$ to about 1200 $m^2/g$.

4. The process for treating mixed hydrocarbon streams of claim 2, wherein said pore volume is within the range of about 0.6 cc/g to about 1 cc/g.

5. The process for treating mixed hydrocarbon streams of claim 2, wherein said surface area is within the range of about 1000–1100 m$^2$/g, and a pore volume of about 0.88 cc/g.

6. The process for treating mixed hydrocarbon streams of claim 2, wherein said carbon is in the form granular carbon or powdered carbon.

7. The process for treating mixed hydrocarbon streams of claim 6, wherein said carbon is granular carbon.

8. The process for treating mixed hydrocarbon streams of claim 6, wherein said carbon is powdered carbon.

9. The process for treating mixed hydrocarbons streams of claim 9, wherein said mixed hydrocarbon stream is in the liquid phase.

10. The process for treating mixed hydrocarbon streams of claim 6, wherein said adsorption conditions comprise a pressure within the range of about 50 psi to about 500 psi.

11. The process for treating mixed hydrocarbon streams of claim 10, wherein said pressure is about 300 psi.

12. The process for treating mixed hydrocarbon streams of claim 6, wherein said contacting comprises passing said stream through a bed of said carbon at a flow rate within the range of about 0.1 LHSV to about 2.0 LHSV.

13. The process for treating mixed hydrocarbon streams of claim 12, wherein said flow rate is about 0.2 LHSV to about 1 LHSV.

14. The process for treating mixed hydrocarbon streams of claim 6, wherein said carbon is used in an amount relative to said stream at a volume ratio within the range of 1:1 to about 1:4000.

15. The process for treating mixed hydrocarbon streams of claim 14, wherein said volume ratio is about 1:500 to 1:1000.

16. The process for treating mixed hydrocarbon streams of claim 2, wherein said carbon is maintained at a temperature within the range of about 10° C. to about 100° C.

17. The process for treating mixed hydrocarbon streams of claim 16,
wherein said temperature is within the range of about 25° C. to about 65° C.

18. The process for treating mixed hydrocarbon streams of claim 2, wherein said polymers have a molecular weight within the range of about 112 gram/mole to about 2500 gram/mole.

19. The process for treating mixed hydrocarbon streams of claim 18, wherein a majority of said polymers have a molecular weight of about 900 gram/mole.

20. The process for treating mixed hydrocarbon streams of claim 2, wherein said amount of said polymers is within the range of about 50 ppm to about 600 ppm.

21. The process for treating mixed hydrocarbon streams of claim 20, wherein said amount of said polymers is within the range of about 50 ppm to about 100 ppm.

22. The process for treating mixed hydrocarbon streams of claim 1, wherein said polymers are selected from the group consisting of polymers of iso-butylene, polymers of the isomers of iso-butylenes and co-polymers of iso-butylene and other olefins.

23. The process for treating mixed hydrocarbon streams of claim 22, wherein said polymers are poly-isobutylenes.

24. The process for treating mixed hydrocarbon streams of claim 23, wherein said reduced amount of said polymers in said resultant stream comprises less than about 5 ppm poly-isobutylenes.

25. The process for treating mixed hydrocarbon streams of claim 24, wherein said reduced amount of poly-isobutylenes in said resultant stream is less than about 1 ppm.

26. The process for treating mixed hydrocarbon streams of claim 25, wherein said hydrocarbon stream is in the liquid phase and said carbon has a surface area within the range of about 50 m$^2$/g to about 200 m$^2$/g and a pore volume within the range of about 0.2 cc/g to about 1.0 cc/g.

27. The process for treating mixed hydrocarbon streams of claim 2, further comprising adding methanol to said resultant stream under conditions and for a time sufficient to produce a product stream comprising methyl-tert-butyl ether and methanol.

28. The process for treating mixed hydrocarbon streams of claim 26, further comprising recovering at least a portion of said methanol from said product stream.

* * * * *